US009360682B1

(12) United States Patent
Edwards

(10) Patent No.: US 9,360,682 B1
(45) Date of Patent: Jun. 7, 2016

(54) CAMERA HEADBAND DEVICE AND SYSTEM WITH ATTACHABLE APPARATUS

(71) Applicant: Remote Xccess, LLC, Laurel, MD (US)

(72) Inventor: Marlena Edwards, Washington, DC (US)

(73) Assignee: Remote Xccess, LLC, Laurel, MD (US)

( * ) Notice: Subject to any disclaimer, the term of this patent is extended or adjusted under 35 U.S.C. 154(b) by 0 days.

(21) Appl. No.: 14/706,900

(22) Filed: May 7, 2015

Related U.S. Application Data

(60) Provisional application No. 61/996,400, filed on May 7, 2014.

(51) Int. Cl.
*G02C 1/00* (2006.01)
*G02C 3/02* (2006.01)
*G02C 11/00* (2006.01)

(52) U.S. Cl.
CPC . *G02C 3/02* (2013.01); *G02C 11/10* (2013.01)

(58) Field of Classification Search
CPC .......... G02C 3/003; G02C 3/02; G02C 11/00; G02C 11/10
USPC ............................................ 351/60, 154, 158
See application file for complete search history.

(56) References Cited

U.S. PATENT DOCUMENTS

| | | | |
|---|---|---|---|
| 6,116,729 A * | 9/2000 | Huang | G02B 25/02 351/158 |
| 7,519,271 B2 | 4/2009 | Strub | |
| 7,576,919 B2 * | 8/2009 | Durner | G02B 23/125 351/158 |
| 8,531,291 B2 | 9/2013 | Tran | |
| 8,593,570 B2 | 11/2013 | Boland | |
| 8,902,315 B2 | 12/2014 | Fisher | |
| 8,934,015 B1 | 1/2015 | Chi | |
| 2004/0005915 A1 | 1/2004 | Hunter | |
| 2006/0055786 A1 | 3/2006 | Ollila | |
| 2012/0229248 A1 | 9/2012 | Parshionikar | |
| 2013/0332073 A1 | 12/2013 | Thomas | |
| 2014/0009606 A1 | 1/2014 | Puccio | |
| 2014/0267799 A1 | 9/2014 | Sadasivam | |
| 2014/0267917 A1 | 9/2014 | Backer | |
| 2014/0347265 A1 | 11/2014 | Aimone | |

* cited by examiner

*Primary Examiner* — Huy K Mai
(74) *Attorney, Agent, or Firm* — Michael D. Eisenberg

(57) ABSTRACT

A headband camera device which transmits streaming video, images, GPS location data and voice communications via a smart phone app or transmit and store data independent of the smart phone app. A Bluetooth module or other short range transmission module in the headband facilitates voice communication by interfacing with a user's Bluetooth enabled smartphone or within a Wifi location. Alternatively, the camera headband device transmits streaming video, sends images and 2-way communications independently of a smartphone over a wireless network by use of an internal SIM card.

12 Claims, 5 Drawing Sheets

CAMERA HEADBAND DEVICE AND SYSTEM WITH ATTACHABLE APPARATUS

CROSS-REFERENCES TO RELATED APPLICATIONS

The present application claims priority from U.S. Provisional Application Ser. No. 61/996,400 filed on May 7, 2014, which is hereby incorporated herein by reference in its entirety.

TECHNICAL FIELD

The present invention, in some embodiments thereof, relates to a camera headband device for capturing and streaming images and video over a network.

BACKGROUND OF THE INVENTION

The present invention relates to a wearable cloud based wireless camera headband that captures and transmits live video, images and/or GPS data to an internet enabled device or remote cloud server. The data can be securely stored to the device and accessed via a smartphone app or computer via the Internet. The wearer can stream live video to share publicly or privately with their inner circle of family, friends, instructor(s), on social networks and verbally communicate with people in real-time. Also, the invention has an input port(s) or cavities at the bottom of the device for attaching an optional lens or useful apparatus such as hands free binoculars; virtual or augmented reality gear which cover the eye(s).

The camera device is held in place by a headband with straps that wrap around both sides of the head to hold the camera in place on the wearer's forehead. An optional light source above the camera enables the wearer the ability to see better in dark conditions. The device also has IR night vision capability. Most importantly, the device's innovation stems from its capability to capture video of what the wearer is seeing, transmit and save this content on the device or to a cloud-based server. Moreover, analytical data can be extracted, processed and shared to and from the device in real-time and on demand via the Internet. Currently, there are no wearable headband devices which do all of the above functions.

BRIEF SUMMARY OF EMBODIMENTS OF THE INVENTION

The present invention relates to a headband camera device which transmits streaming video images; GPS location data and voice communications via a smart phone app or can transmit and store data independent of the smart phone app. A Bluetooth module or other short range transmission module in the headband facilitates voice communication by interfacing with a user's Bluetooth enabled smartphone or within a Wifi location. Furthermore this invention is a Wi-Fi enabled device platform.

Alternatively, the camera headband device transmits streaming video, sends images and 2-way communications independently of a smartphone over a wireless network by use of an internal SIM card.

The camera headband device is designed with an emphasis on protecting the privacy of the general public. Secure encryption methods and algorithms protect highly sensitive data and mitigate against hacking and cyber-attacks. The integrated Central Processing Unit (CPU) enables the device to send and receive extracted insightful information from various data sets while interfacing with secure database(s).

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

Figure 1:
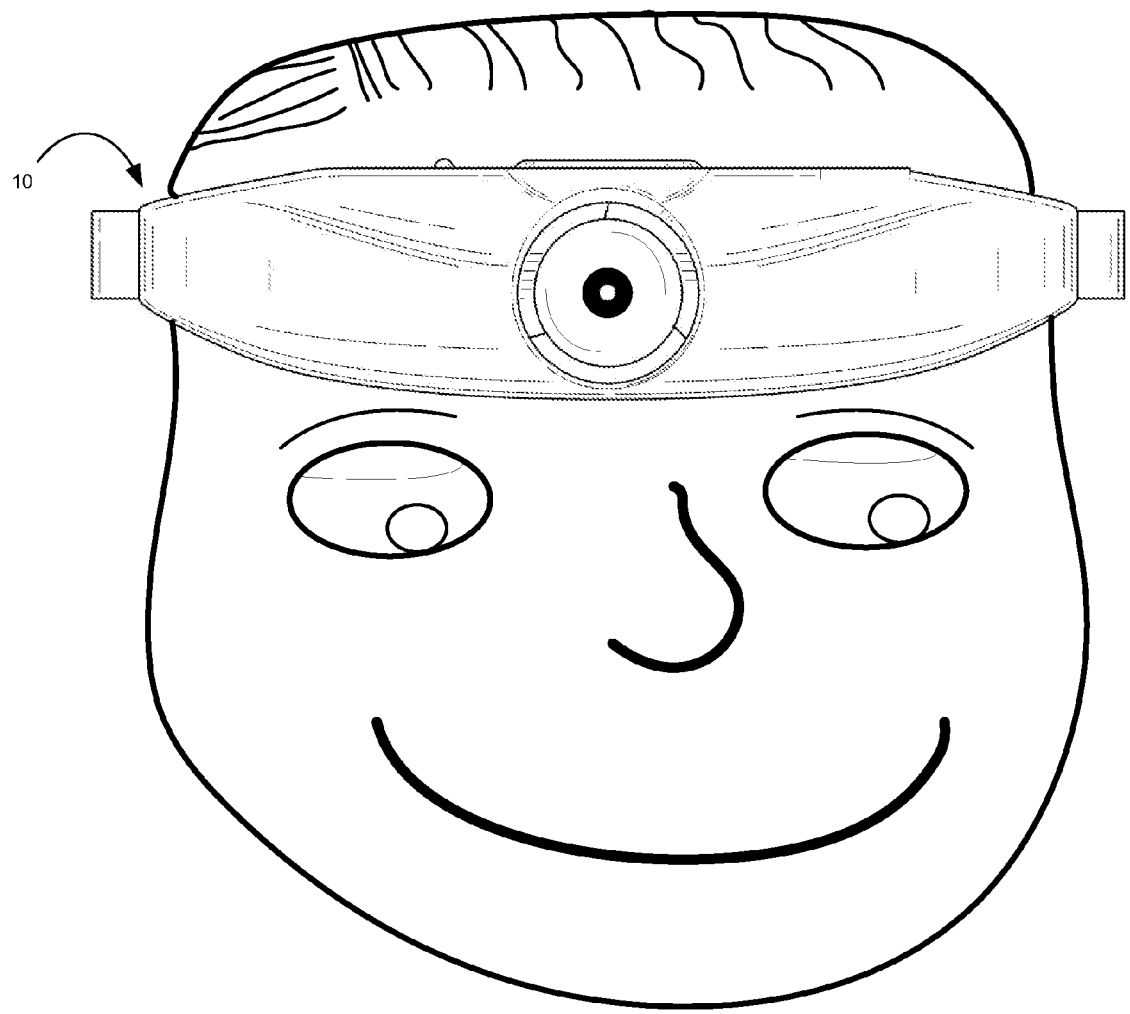
FIG. 1 is a perspective view of the camera headband device being worn by a user.
Figure 2:
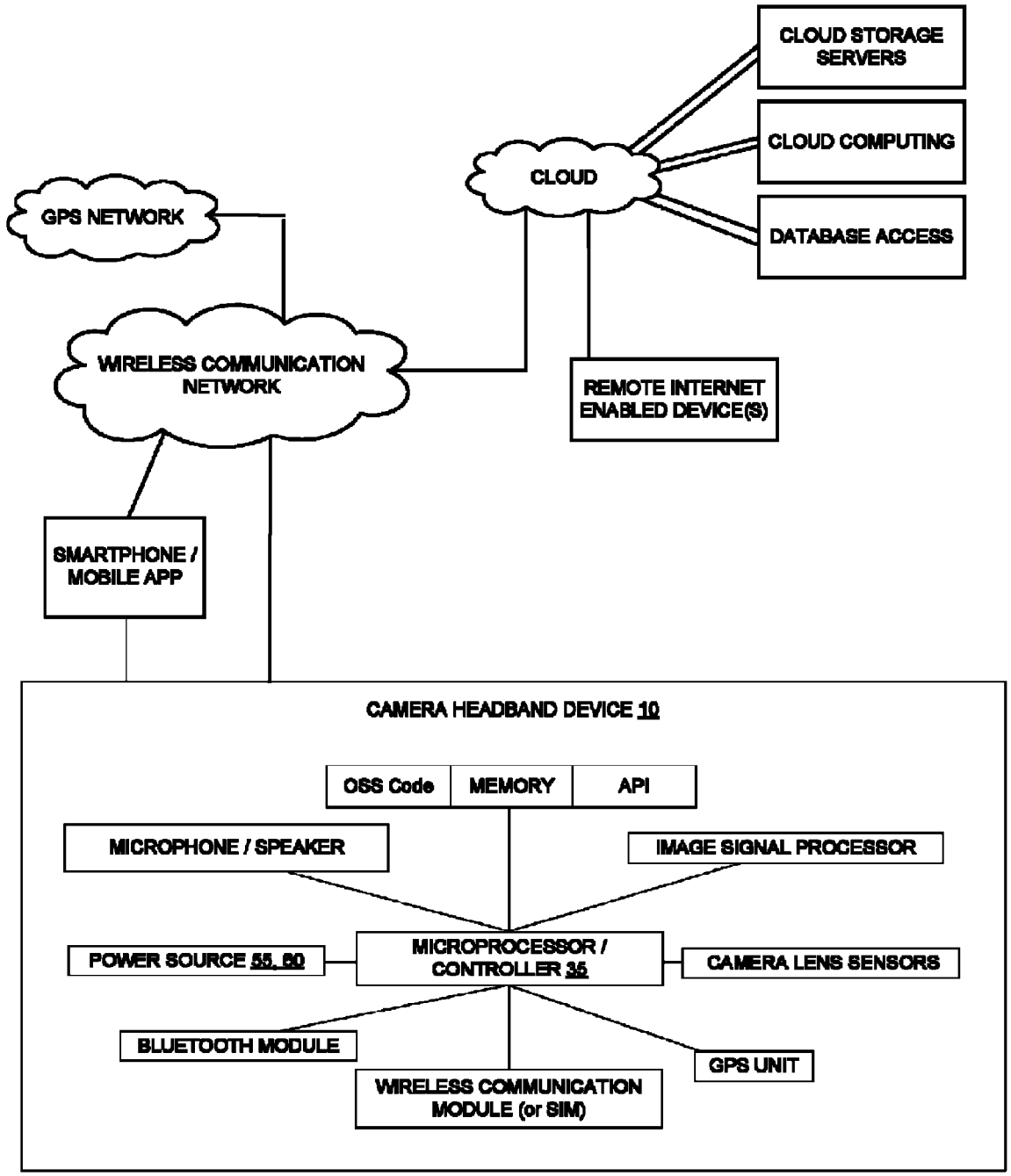
FIG. 2 is a block diagram of the camera headband device and system.
Figure 3:
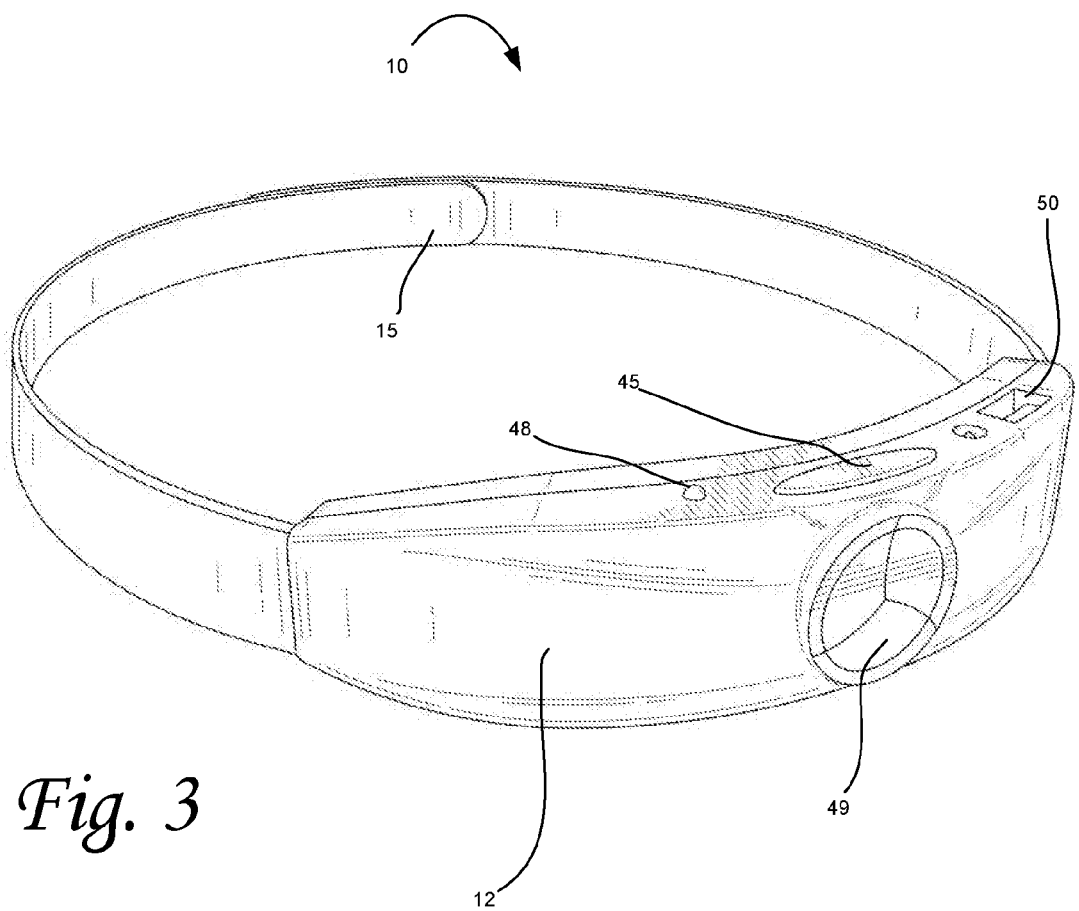
FIG. 3 is a is a perspective view of the camera headband device with the lens lid in a closed position.
Figure 4:
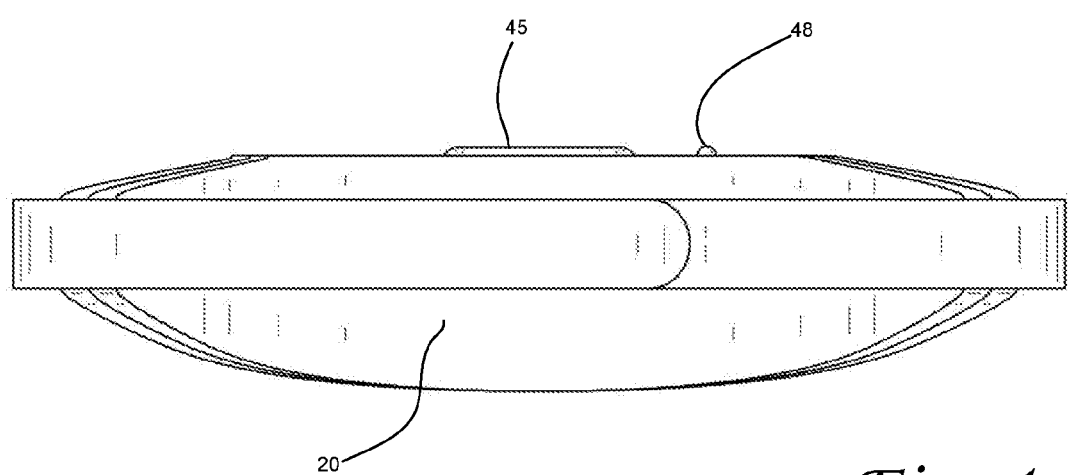
FIG. 4. is a rear view of the camera headband device.
Figure 5:
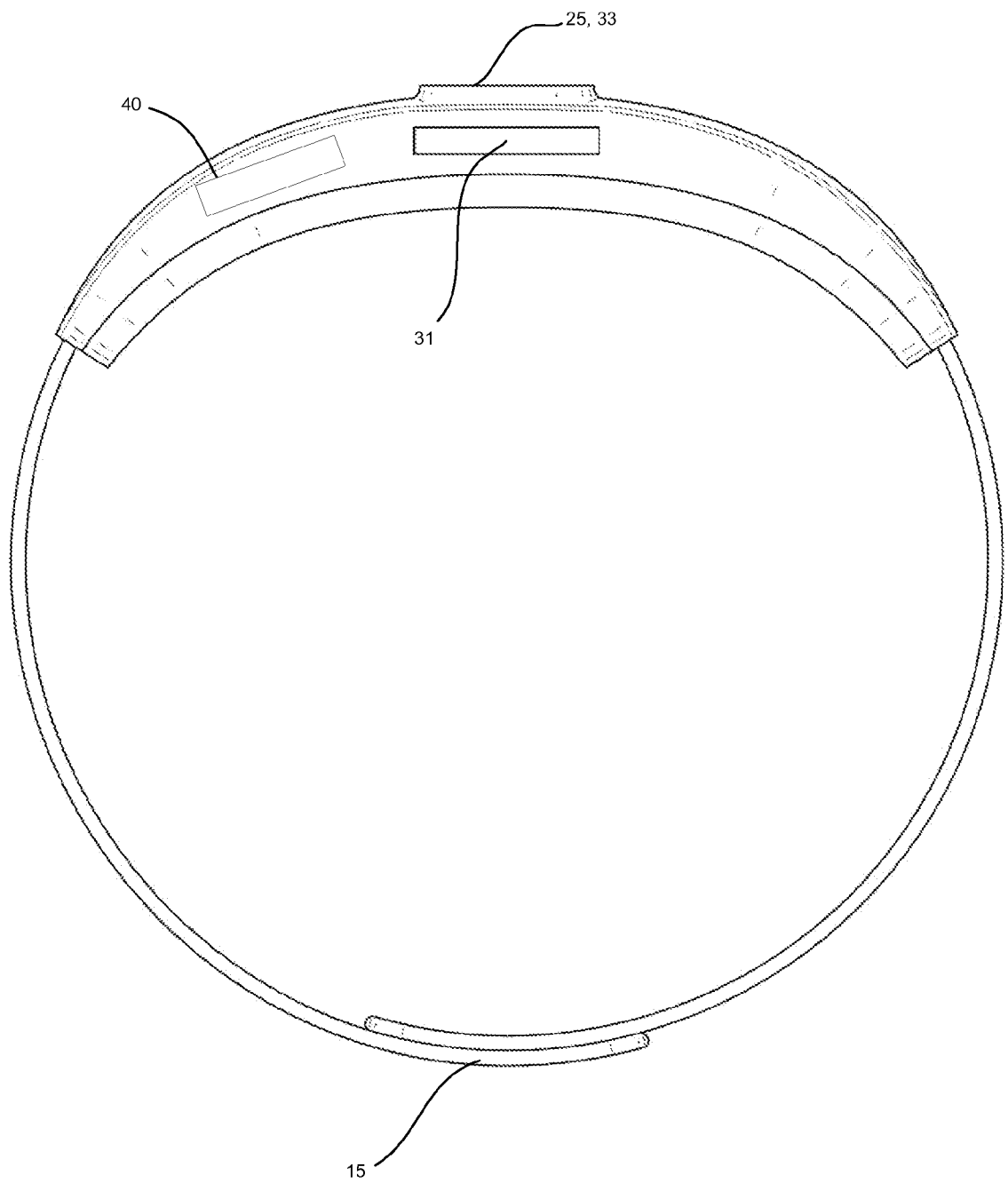
FIG. 5 is a top view of the camera headband device.
Figure 6:
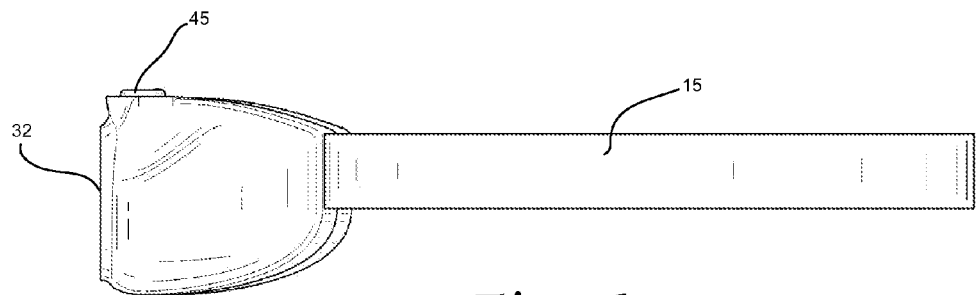
FIG. 6 is a side view of the camera headband device.
Figure 7:
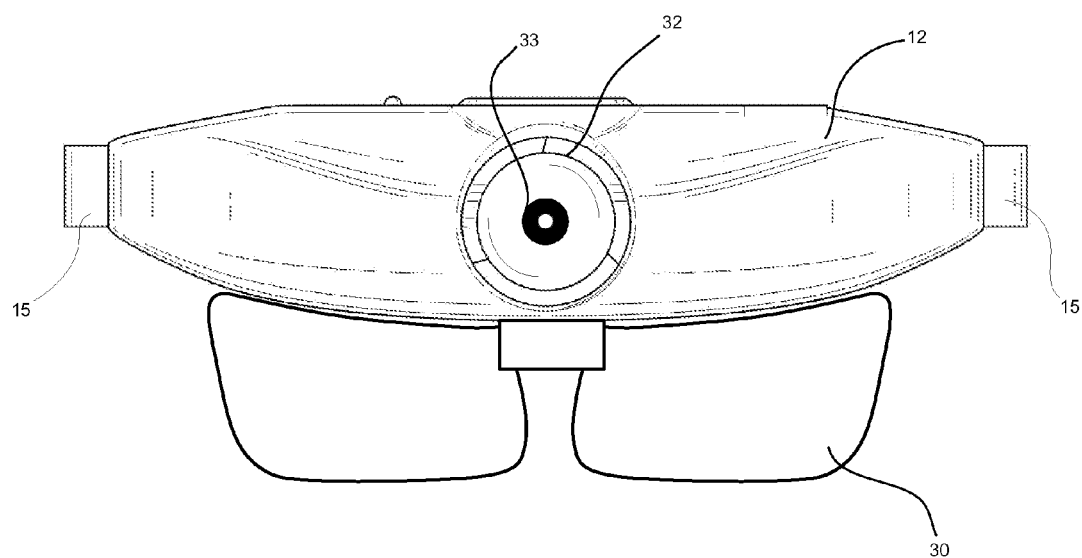
FIG. 7 is a front view of the camera headband device with the lens lid in an open position and an attachable lens connected via a port.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

The following reference numerals are used throughout this document:
- 10 camera headband device;
- 12 housing;
- 15 fastener;
- 20 sweat resistant inner cushion;
- 25 camera;
- 30 lens;
- 31 port;
- 32 circular opening;
- 33 camera lens;
- 35 microprocessor
- 40 cavity;
- 45 on/off button;
- 48 LED indicators;
- 49 lens lid;
- 50 USB port;
- 55 rechargeable lithium-ion battery;
- 60 UL;

Referring to FIGS. 1-7, the present invention, in some embodiments thereof, relates to a camera headband device 10. Referring to FIG. 1, the camera headband device 10 has a housing 12 that is curved and generally shaped to fit against the forehead of a person and is secured by attaching both ends at the back of a user's head using a fastener 15 such as Velcro® or a buckle. The camera headband 10 may be waterproof and may have a sweat resistant inner cushion 20. The camera headband device 10 is configured for attachment to a lens, binoculars and virtual reality apparatus below a camera 25 which extends over the user's eye(s). An attachable lens 30 or apparatus is configured to interface with the camera headband device's microprocessor 35 or independent of it and is utilized for a variety of applications. The lens 30 interfaces via a port 31 on a bottom side of the device 10. The various applications transmit analytical data through interfacing with the camera headband device's circuit board. Developers can create applications for the attachable lens or apparatus to further the advancement of the invention and its beneficial use for humans. Also, the attachable apparatus and applications can pertain to augmented or virtual reality devices which are customized to fit the invention.

The lens 30 has microscopic visual sensors which accurately track the movement of the wearer's pupil(s) to coincide with the movement of a camera lens 33 disposed in a circular opening 32 in the housing 12. Thus, anywhere the wearer's eye moves, the integrated camera moves and captures video streams which are stored on the device or in a distant database server in network communication with the camera headband device 10.

In another variant, the attachable lens 30 or apparatus displays useful information sent remotely from another person(s), or data from the Internet or a database to the wearer, which may be beneficial for learning and instructional purposes. Another optional attachable apparatus has biometric scanning sensors which enable the wearer's iris to be scanned to authenticate their identity. The biometric scanner can be used for secure identification such as payment processing and secret clearance to access a secure data networks online and offline.

Another useful application of the attachable biometric apparatus can examine the wearer's eyes. For example, doctors can perform a remote eye examination in real-time of a patient's eyes by wearing the camera headband device. Doctors have immediate access to determine the diagnosis of their patient's eyes via precise imagery and analytical data captured and securely transmitted via the Internet. More importantly, the camera headband device can mine data from the Internet and/or various medical databases to quickly perform comparative analysis of a patient's digital images of their eyes to detect a potential disease.

Additionally, the camera headband device responds to voice commands and has artificial intelligence to access online search results and/or retrieve data which can be formatted to display on the attachable lens. The CPU or microprocessor/circuit board 35 may optionally be made of flexible silicon with internal over-the-air (OTA) programming firmware that can be updated via cloud or USB connection.

The camera headband device's camera lens 33 can be developed to capture video up to a 180 degree angle with night vision and/or infrared capability. An authorized remote user(s) can operate a PC, tablet or mobile app to make the camera pan, tilt and zoom in and out on an object. The camera headband device optionally has a facial and/or retina recognition application for identifying a person(s).

The camera headband device has a USB port 50 for charging and transferring data stored to a PC, or smartphone. The camera headband device may be powered by a rechargeable lithium-ion battery 55, micro USB, UL 60 cord or solar power. The device 10 has a memory module and a short and long range wireless communication modules. Optionally, the device has open source software stored in memory. Optionally the device 10 has an application program interface stored in memory and is capable of being interfaced by a smartphone via the short range wireless communication module. In one embodiment, the short range wireless communication module is Bluetooth based.

The camera headband device has an on/off button 45 and LED indicators 48 which display full or low charge. The camera headband device has an optional button to snap images to be stored on the device or to the cloud. When the camera headband device is powered on the device 10 has a lens lid 49 covering the camera lens that automatically opens and may be configured to cover the lens when the device 10 is powered off. Alternatively, the device may have 3 settings where the power button is located. One setting is to turn on the camera headband device which automatically opens the camera lid, the second setting is to close the lid without turning off the camera headband device and the third setting is to power off the device and close the lens lid.

In another variant, the optional attachable lens 30 or apparatus is inserted in a cavity 40 located at the bottom of camera headband device or attached via another connection method on both sides; one side or any part of the bottom of the camera headband device.

Another useful application of the camera headband device involves the enhancement of instructional education of people across the world. For instance, the wearer could learn how to replace a part on their vehicle by enabling a certified mechanic to provide step-by-step real-time instructions on how the part should be replaced. The mechanic is seeing what the wearer is seeing which eliminates or reduces mistakes. Medical students across the globe can access live video of a surgeon wearing the invention while performing any number surgical procedures and see firsthand how a medical procedure is done.

Military soldiers can greatly benefit from wearing the invention during dangerous missions in hostile territories. Soldiers wearing the camera headband device can transmit real-time reconnaissance video and location data and receive instructions from superior officers or remote a command center on how to proceed. The police departments equipping their officers with the camera headband device can remotely access video of dangerous hostage situations to more effectively strategize to mitigate against the loss of lives. One of the essential benefits of the camera headband device when worn by military and police is their hands are free to hold a weapon or quickly access their weapon. Also, the ability to capture and store real-time video is extremely valuable for evidence. Millions of consumers wearing the camera headband device will enjoy sharing live video of captivating vacation scenes with family and friends via the internet and social networks. Extreme sports participants can wear the camera headband device to capture and stream their adventurist stunts to be access by friends and family in real-time. Businesses can equip employees with the camera headband device to enable collaborative participation to expedite the completion of creative projects or research and development in real-time.

In addition, the camera headband device may have an optional attachable virtual reality apparatus to enable the wearer to have a more immersive learning or gaming experience. The optional attachable hands-free binoculars can assist the wearer to zoom in on people, objects or locations while streaming and/or storing live video of what the wearer views.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A wireless camera headband device, comprising:
a housing with two ends attached to a strap at each end, conforming generally to a human forehead;
a camera lens disposed within an opening in the housing for the camera lens;
a lens lid connected to the housing, and configured to completely occlude the opening in the housing for the camera lens, wherein the lens lid is configured to cover the opening or reveal the opening for use;
a memory module;
a wireless communication module; and
a CPU processor in electrical communication with the camera lens, memory module and wireless communication module, and operable to capture photographs and/or video through the camera lens and store the photographs and/or video in the memory and/or transmit the data over a wireless communication network to a remote server or database.

2. The camera headband device of claim 1, further comprising disposed in the housing:
  a USB port;
  an LED;
  a power on/off button;
  a port disposed in a bottom side of the housing configured for receiving an attachable lens or auxiliary apparatus.

3. The camera headband device of claim 2, wherein the power on/off button comprises a setting that causes the lens lid to close over the lens and the camera headband device remains powered on.

4. The camera headband device of claim 2, wherein the auxiliary apparatus is a binoculars.

5. The camera headband device of claim 2, wherein the auxiliary apparatus is a virtual or augmented reality apparatus.

6. The camera headband device of claim 2, further comprising an attachable lens configured to interface with the processor via a port on the camera headband device, the attachable lens having visual sensors configured to track the movement of a wearer's pupils to coincide with the movement of the camera lens, wherein anywhere the wearer's eye moves, the camera lens moves and captures video streams which are stored in a distant database in network communication with the camera headband device.

7. The camera headband device of claim 2, further comprising a sweat resistant inner cushion.

8. The camera headband device of claim 1, further comprising:
  a microphone;
  a power source;
  a short range wireless communication module for interfacing with a smartphone;
  an image signal processor;
  a GPS unit;
  biometric scanning sensors;
  wherein the memory module is computer readable memory having instructions stored thereon, comprising one or more of:
    open source code; and
    application program interface;
    wherein when the computer readable instructions are executed by the processor, they are operable to cause the camera headband device to acquire biometric data through the lens and transmit the data over the wireless communication network via a smartphone app.

9. The camera headband device of claim 8, wherein the camera headband device is operable via a smartphone.

10. The camera headband device of claim 1, wherein the strap comprises two sections, that overlap and adhere via hook and loop to form an enclosure around a wearer's head.

11. A camera headband device, comprising:
  a housing with two ends attached to a strap at each end, conforming generally to a human forehead;
  a camera lens disposed within an opening in the housing for the camera lens;
  a lens lid connected to the housing, and configured to completely occlude the opening in the housing for the camera lens, wherein the lens lid either automatically opens or covers the opening or is manually configurable by a user to cover the opening or reveal the opening for use;
  a memory module;
  a wireless communication module; and
  a processor in electrical communication with the camera lens, memory module and wireless communication module, and operable to capture photographs and video through the camera lens and store image data in the memory and transmit the image data over a wireless communication network to a database;
  wherein disposed in the housing, the camera headband comprises:
    a USB port;
    an LED;
    a power on/off button;
    a sweat resistant inner cushion;
    a port disposed in a bottom side of the housing configured for receiving an attachable lens or auxiliary apparatus;
    a microphone;
    a power source;
    a short range wireless communication module for interfacing with a smartphone;
    an image signal processor;
    a GPS unit;
    biometric scanning sensors;
  an attachable lens configured to interface with the processor via a port on the camera headband device, the attachable lens having visual sensors configured to track the movement of a wearer's pupils to coincide with the movement of the camera lens, wherein anywhere the wearer's eye moves, the camera lens moves and captures video streams which are stored in a distant database in network communication with the camera headband device;
  wherein the memory module is computer readable memory having instructions stored thereon, wherein when the computer readable instructions are executed by the processor, they are operable to cause the camera headband device to acquire biometric data through the lens and/or transmit the data over the wireless communication network via a smartphone app.

12. A wireless camera headband device, comprising:
  a housing with two ends attached to a strap at each end, conforming generally to a human forehead;
  a camera lens disposed within an opening in the housing for the camera lens;
  a lens lid connected to the housing, and configured to completely occlude the opening in the housing for the camera lens, wherein the lens lid is configured to cover the opening or reveal the opening;
  a port disposed on a bottom of the housing configured for receiving an attachable lens or auxiliary apparatus, and connecting the apparatus to the camera headband device;
  a memory module;
  a wireless communication module; and
  a CPU processor in electrical communication with the camera lens, memory module and wireless communication module, and operable to capture photographs and/or video through the camera lens and store the photographs and/or video in the memory and/or transmit the data over a wireless communication network to a remote server or database.

* * * * *